United States Patent
Vinski et al.

[11] Patent Number: 6,030,931
[45] Date of Patent: Feb. 29, 2000

[54] FOAMING CLEANSING SKIN PRODUCT

[75] Inventors: Paul Vinski, Danbury; Alexander Paul Znaiden, Trumbull; Craig Stephen Slavtcheff, Guliford, all of Conn.

[73] Assignee: Chesebrough-Pond's USA Co., Division of Conopco, Inc., Greenwich, Conn.

[21] Appl. No.: 09/017,746

[22] Filed: Feb. 3, 1998

[51] Int. Cl.[7] ................................ C11D 1/94; C11D 17/00
[52] U.S. Cl. .................. 510/130; 510/140; 510/155; 510/406; 510/421; 510/433; 510/501; 510/502; 510/504; 424/401; 514/844; 239/330; 239/343; 239/575; 239/590.3
[58] Field of Search ...................... 510/140, 155, 510/406, 130, 421, 433, 501, 502, 504; 424/401; 514/844; 239/330, 343, 575, 590.3

[56] References Cited

U.S. PATENT DOCUMENTS

| | | | |
|---|---|---|---|
| 3,728,447 | 4/1973 | Osipow et al. | 424/70 |
| 5,093,112 | 3/1992 | Birtwistle et al. | 424/70 |
| 5,139,781 | 8/1992 | Birtwistle et al. | 424/401 |
| 5,364,031 | 11/1994 | Taniguchi et al. | 239/330 |
| 5,462,208 | 10/1995 | Stahley et al. | 222/207 |
| 5,490,955 | 2/1996 | Hagan et al. | 434/70.22 |
| 5,599,549 | 2/1997 | Wivell et al. | 424/401 |
| 5,635,469 | 6/1997 | Fowler et al. | 510/406 |

FOREIGN PATENT DOCUMENTS 9117237  11/1991  WIPO .

*Primary Examiner*—Lorna Douyon
*Attorney, Agent, or Firm*—Milton L. Honig

[57] ABSTRACT

A foaming cleansing product is provided as a cleansing composition packaged in a non-aerosol mechanical dispenser. The dispenser includes a container for holding a liquid composition, a dispensing head with a housing enclosing a pump mechanism and a screen material in the flow path to convert liquid composition into a foam, and a diptube for delivering liquid from the container to the dispensing head. The cleansing composition is free of water insoluble emollients and includes an anionic surfactant and an amphoteric surfactant of structure:

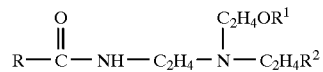

wherein R is a fatty alkyl of 6 to 22 carbons; $R^1$ is selected from the group consisting of H, $C_2H_4COOH$ and $C_2H_4COONa$; and $R^2$ is selected from the group consisting of $COONa$, $CH_2CHOHCH_2SO_3Na$, $C_2H_4COONa$, $CH_2COOCH_2COOH$ and $CH_2COOCH_2COONa$.

6 Claims, No Drawings

FOAMING CLEANSING SKIN PRODUCT

BACKGROUND OF THE INVENTION

1. Field of the Invention

The invention concerns a foaming cleansing product which is a combination of a non-aerosol dispenser and a cleansing composition designed to cooperate with the dispenser for generating a mousse quality foam while concurrently imparting moisturization benefits to the skin.

2. The Related Art

Cleansing compositions in mousse form have certain appeal to consumers. Foremost is the instant foam achieved by the mere press of a button. Aerosol dispensers employing propellants generally provide a satisfactory foam volume. Unfortunately, aerosol products are under attack for environmental reasons. Volatile organics interfere with the earth's ozone layer and contribute to smog in metropolitan areas. Aerosol packages are also relatively costly to assemble. For all these reasons, attention has been recently directed at non-aerosol dispensers.

U.S. Pat. No. 5,635,469 (Fowler et al.) discloses personal cleansing products comprising a foamable liquid composition and a foam-producing non-aerosol dispenser. The compositions include a surfactant, a water soluble cationic or nonionic polymer, a humectant, a water-insoluble emollient and water. The dispenser employs at least two screens through which the composition is blown to generate a foam.

Delivery of cleansing compositions via non-aerosol dispensers has presented many challenges. Foams produced from these dispensers often lack the dense volume consumers desire. These foams also may not be long lasting or luxurious. Additives within these compositions intended to deliver skin benefit agents can interfere with the foam properties. Still further, certain types of non-aerosol dispensers which operate with porous filters or meshed screens require the cleansing product to be relatively non-viscous. Where the package is transparent, formulators seek clear formulations for aesthetics purposes.

Accordingly, it is an object of the present invention to provide a cleansing product in mousse form which delivers a dense luxurious foam.

Another object of the present invention is to provide a cleansing product in mousse form which delivers benefit agents to the skin that do not interfere with foam properties.

Still another object of the present is to provide a cleansing product in mousse form having a transparent liquid formulation.

These and other objects of the present invention will become more readily apparent from consideration of the summary and detailed description which follows.

SUMMARY OF THE INVENTION

A foaming cleansing product is provided which includes:

(A) a non-aerosol dispenser having:
 (i) a container for storing a cleansing composition;
 (ii) a head having a housing surrounding a pump mechanism and a foam-forming screen material;
 (iii) a diptube communicating between the container and head functioning to fluidly deliver liquid cleansing composition between container and head and being upstream from the screen material; and
(B) the cleansing composition being free of water insoluble emollients and including:
 (i) from 0.1 to 50% by weight of an anionic surfactant; and
 (ii) from 0.1 to 30% by weight of an amphoteric surfactant having the structure:

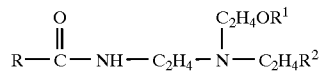

wherein R is a fatty alkyl of 6 to 22 carbons; $R^1$ is selected from the group consisting of H, $C_2H_4COOH$ and $C_2H_4COONa$; and $R^2$ is selected from the group consisting of $COONa$, $CH_2CHOHCH_2SO_3Na$, $C_2H_4COONa$, $CH_2COOCH_2COOH$ and $CH_2COOCH_2COONa$.

DETAILED DESCRIPTION

Now it has been discovered that a rich, luxurious creamy foam can be generated through a non-aerosol mechanical pump by a cleansing system based on anionic surfactants and an amphoteric surfactant having the structure:

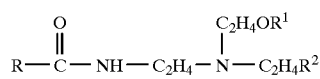

wherein R is a fatty alkyl of 6 to 22 carbons; $R^1$ is selected from the group consisting of H, $C_2H_4COOH$ and $C_2H_4COONa$; and $R^2$ is selected from the group consisting of $COONa$, $CH_2CHOHCH_2SO_3Na$, $C_2H_4COONa$, $CH_2COOCH_2COOH$ and $CH_2COOCH_2COONa$.

Specific examples of these amphoteric surfactants include the alkali, alkaline earth, ammonium and trialkanolammonium salts of cocoamphoacetate, cocoamphodiacetate, cocoamphopropionate, cocoamphodipropionate and mixtures thereof. Most preferred is sodium cocoamphoacetate available as Miranol HMA from the Rhone Poulenc Corporation. Similar surfactants are also available as Amphoterge® from Lonza Inc., Fair Lawn, N.J. While the sodium salt is preferred, other cations can also be employed including lithium, potassium, magnesium and calcium. Amounts of the amphoteric surfactant may range from 0.1 to 20%, preferably from 1 to 10%, optimally from 2 to 6% by weight.

A further component of cleansing compositions according to the present invention is that of an anionic surfactant. Illustrative but not limiting examples include the following classes:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3$—$M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3-M+)CO_2R^2$ where $R^1$ is straight or branched alkyl from about $C_8$ to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

Co-surfactants may also be present to aid in the foaming, detergency and mildness properties. Nonionic and amphoteric actives are the preferred co-surfactants. Suitable nonionic surfactants include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethyldodecylamine oxide, oleyldi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecoxy-2-hydroxypropyldi(3-hydroxypropyl)amine oxide, and dimethylhexadecylamine oxide.

Amounts of the nonionic surfactant may range from 0.1 to 40%, preferably from 0.5 to 15%, optimally from 1 to 5% by weight of the total composition.

Amphoteric surfactants such as betaines may also be employed as co-actives along with the anionic surfactants. Suitable betaines may have the general formula $RN^+(R^1)_2R^2COO-$ wherein R is a hydrophobic moiety selected from the group consisting of alkyl groups containing from 10 to 22 carbon atoms, preferably from 12 to 18 carbon atoms; alkyl aryl and aryl alkyl groups containing 10 to 22 carbon atoms with a benzene ring being treated as equivalent to about 2 carbon atoms, and similar structures interrupted by amido or ether linkages; each $R^1$ is an alkyl group containing from 1 to 3 carbon atoms; and $R^2$ is an alkylene group containing from 1 to about 6 carbon atoms. Sulfobetaines such as cocoamidopropyl sultaine are also suitable.

Examples of preferred betaines are dodecyl dimethyl betaine, cetyl dimethyl betaine, dodecyl amidopropyldimethyl betaine, tetradecyldimethyl betaine, tetradecylamidopropyldimethyl betaine, and dodecyldimethylammonium hexanoate. Most preferred is cocoamidopropyl betaine available as Tegobetaine F® sold by Th. Goldschmidt AG of Germany. Amounts of the betaine may range from 0.05 to 15%, preferably from 0.5 to 10%, optimally from 2 to 8% by weight of the total composition.

Moisturizing ingredients may also be included in compositions of the present invention. Water soluble moisturizers such as polyhydric alcohol-type humectants are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from 0.5 to 30%, preferably between 1 and 15% by weight of the composition.

Compositions of the present invention preferably are free of any oil phase, especially free of water insoluble emollients. The term "free" means less than 0.05%, preferably less than 0.01% emollient, and water insoluble means any emollient having a solubility in distilled water at 25° C. of less than about 1 gm per 100 mL, more preferably less than about 0.1 gm per 100 mL. Absent water insoluble emollients, the compositions can be transparent and have improved foamability.

Preservatives can desirably be incorporated into the cosmetic compositions of this invention to protect against the growth of potentially harmful microorganisms. Suitable traditional preservatives are EDTA salts and alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Minor adjunct ingredients may be present in the cosmetic compositions. Among them may be the water-soluble vitamins, colorants, fragrances and opacifiers. Each of these substances may range from 0.05 to 5%, preferably between 0.1 and 3% by weight.

Advantageously, the compositions of the invention may contain a foam densifying agent. Examples of this substance are waxy materials with a melting point greater than 20° C., preferably greater than 40° C. Illustrative are ethoxylated glyceride esters such as PEG 75 soy glycerides sold under the trademark Acconon S 75. Also useful are $C_8$–$C_{12}$ acyl lactylates such as sodium lauroyl lactylate sold as Pationic 138 C® available from the Patterson Chemical Company. Amounts of these agents may range from 0.1 to 10%, preferably from 0.5 to 5%, optimally from 1 to 3% by weight.

Cationic conditioning agents in monomeric and polymeric type are also useful for purposes of this invention.

Examples of the polymeric type include: cationic cellulose derivatives, cationic starches, copolymers of a diallyl quaternary ammonium salt and an acryl amide, quaternized vinylpyrrolidone vinylimidazole polymers polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16, etc. manufactured by the Celanese Company), quaternary ammonium salt polymers (e.g. Mirapol A-15, Mirapol AD-1, Mirapol AZ-1, etc., manufactured by the Miranol Divison of the Rhone Poulenc Company). Most preferred is polyquaternium-11 available as Luviquat® PQ 11 sold by the BASF Corporation.

Examples of monomeric cationic conditioning agents are salts of the general structure:

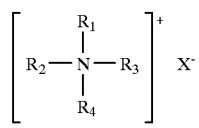

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carton atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicones quats may similarly be employed. Most preferred is Silquat AD designated by the CTFA as Silicone Quaternium 8, available from Siltech Inc.

Amounts of each cationic agent may range from 0.05 to 5%, preferably from 0.1 to 3%, optimally from 0.3 to 2.5% by weight.

Advantageously the compositions of this invention are transparent. By the term transparent is meant having a maximum transmittance of light of at least 4% of any wave length in the range of 400 to 700 nm through a sample 1 cm thick. A transparent composition is one which also permits sufficient light transmittance to enable reading of newspaper print through a thickness commensurate with a diameter of the container employed with the herein described dispenser.

Compositions of this invention should also be of relatively low viscosity to be pumpable. Viscosity may range from 1 to 300 centipoise, preferably from 3 to 100 centipoise, optimally from 5 to 50 centipoise at 25° C.

An essential element of cleansing products according to this invention is a non-aerosol mechanical dispenser. The dispenser is generally characterized by a container for storing the composition (preferably a transparent container), a dispensing head defined by a housing containing a pump, and a diptube for transferring the composition from the container into the dispensing head. Foam is created by requiring the composition to pass through a screen material which may be a porous substance such as a sintered material, a wire (plastic or metal) gauze screen or similar structures.

Suitable dispensers are described in U.S. Pat. No. 3,709,437 (Wright), U.S. Pat. No. 3,937,364 (Wright), U.S. Pat. No. 4,022,351 (Wright), U.S. Pat. No. 4,147,306 (Bennett), U.S. Pat. No. 4,184,615 (Wright), U.S. Pat. No. 4,598,862 (Rice), U.S. Pat. No. 4,615,467 (Grogan et al.) and U.S Pat. No. 5,364,031 (Tamiguchi et al.). Most preferred however is a device owned by the Airspray International Corporation described in WO 97/13585 (Van der Heijden). All these patents are incorporated herein by reference. The Airspray device comprises a container for storing a cleansing composition and a dispensing head, the latter including at least a concentric air pump and liquid pump. Each of the pumps has a piston chamber with a piston displaceable therein and an inlet and discharge, and an operating component for operating the two pumps. The operating component is integral with one of the pistons and comprises an outflow channel with a dispensing opening. Shut-off mechanisms, rendering it possible to suck up air or liquid, respectively, and dispense them, are present in the inlet and discharge of the pumps. The air pump includes a double-acting shut-off device which can be operated actively by the operating component. The shut-off device prevents both the inlet of air to the air pump and discharge of air therefrom. The air piston is able to be moved freely at least over a small distance with respect to the operating component.

The following examples will more fully illustrate the embodiments of this invention. All parts, percentages and proportions referred to herein and in the appended claims are by weight unless otherwise indicated.

EXAMPLES 1–8

The following examples are representative cleansing formulations according to the present invention.

|  | EXAMPLE | | | | | | | |
| --- | --- | --- | --- | --- | --- | --- | --- | --- |
| COMPONENT | 1 | 2 | 3 | 4 | 5 | 6 | 7 | 8 |
| Phase A | (WEIGHT %) | | | | | | | |
| Pationic 138C (sodium lauroyl lactylate) | 1.00 | 1.00 | 1.00 | 1.00 | 1.00 | 1.00 | 1.00 | 1.00 |
| Glycerin | 3.00 | 3.00 | 3.00 | 3.00 | 3.00 | 3.00 | 3.00 | 3.00 |
| Luviquat PQ 11 (Polyquaternium 11) | 0.90 | 0.60 | 0.60 | 0.50 | 0.30 | 1.50 | 1.50 | 1.50 |

-continued

| COMPONENT | EXAMPLE | | | | | | | |
|---|---|---|---|---|---|---|---|---|
| | 1 | 2 | 3 | 4 | 5 | 6 | 7 | 8 |
| Luviquat Mono CP (Hydroxyethyl cetylammonium phosphate) | 2.00 | 1.50 | 2.50 | 2.00 | 0.80 | 3.00 | 3.00 | 4.00 |
| Glydant Plus (DMDM Hydantion + iodopropynyl butylcarbamate). | 0.10 | 0.10 | 0.10 | 0.10 | 0.10 | 0.10 | 0.10 | 0.10 |
| Acconon S75 (PEG 75 soy glycerides) | 1.00 | 1.00 | 1.00 | 1.00 | 1.00 | 1.00 | 1.00 | 1.00 |
| Silquat AD | 2.00 | — | 1.50 | 2.00 | 2.00 | 2.00 | 1.50 | 0.50 |
| Water | qs | qs | qs | qs | qs | qs | qs | qs |
| Phase B | | | | | | | | |
| Standapol ES-2 (SLES 28%) | 8.00 | 8.00 | 8.00 | 6.00 | 6.00 | 6.00 | 6.00 | 6.00 |
| Crillet 80 (Polysorbate 80) | 2.00 | 2.00 | 2.00 | 2.00 | 2.00 | 2.00 | 2.00 | 2.00 |
| Bioterge AS 40 (sodium C14–16 olefin sulphonate) | 8.00 | 8.00 | 8.00 | 6.00 | 6.00 | 6.00 | 6.00 | 6.00 |
| Tegobetaine F (Cocoamidopropyl betaine) | 8.00 | 8.00 | 8.00 | 6.00 | 6.00 | 6.00 | 6.00 | 6.00 |
| Miranol HMA (sodium lauroamphoacetate 30%) | 12.67 | 10.42 | 10.42 | 12.67 | 12.67 | 8.35 | 8.35 | 15.39 |
| Phase C | | | | | | | | |
| Tween 80 | 0.15 | 0.15 | 0.15 | 0.15 | 0.15 | 0.15 | 0.15 | 0.15 |
| Fragrance | 0.15 | 0.15 | 0.15 | 0.15 | 0.15 | 0.15 | 0.15 | 0.15 |
| Colorant | 0.03 | 0.03 | 0.03 | 0.03 | 0.03 | 0.03 | 0.03 | 0.03 |

These formulas are prepared by charging water to form Phase A in a main vessel. Heating is then begun to achieve a 50° C. temperature. Pationic 138C® is then added and allowed to slowly dissolve. The remaining ingredients listed under Phase A are added and allowed to dissolve. Heating and stirring are continued until a uniform mixture is obtained. Thereafter Phase A is cooled. Phase B ingredients are then added to Phase A with slow agitation to minimize aeration. Stirring is continued until the mixture becomes uniform. Premix Phase C is then added to the resultant mixture at 35° C.

EXAMPLES 9–18

The following examples demonstrate the effect of changing surfactants and additives on the foam and skinfeel properties.

| COMPONENT | EXAMPLE | | | | | | | | | |
|---|---|---|---|---|---|---|---|---|---|---|
| | 9 | 10 | 11 | 12 | 13 | 14 | 15 | 16 | 17 | 18 |
| Phase A | | | | | | | | | | |
| Pationic 138C (sodium lauroyl lactylate) | — | — | — | — | — | — | 1.00 | — | 1.00 | — |
| Acconon S75 (PEG 75 soy glycerides) | — | — | — | — | — | — | — | 1.00 | 1.00 | — |
| Silquat AD | — | — | — | — | — | — | — | — | — | 1.00 |
| Water | 90.00 | 90.00 | 90.00 | 90.00 | 90.00 | 80.00 | 79.00 | 79.00 | 78.00 | 79.00 |
| Phase B | | | | | | | | | | |
| Standapol ES-2 (SLES 28%) | 10.00 | — | — | — | 5.00 | 5.00 | 5.00 | 5.00 | 5.00 | 5.00 |
| Bioterge AS 40 (sodium C14–16 olefin sulphonate) | — | 10.00 | — | — | 5.00 | 5.00 | 5.00 | 5.00 | 5.00 | 5.00 |
| Tegobetaine F (Cocoamidopropyl betaine) | — | — | 10.00 | — | — | — | — | — | — | — |
| Miranol HMA (sodium lauroamphoacetate 30%) | — | — | — | 10.00 | — | 10.00 | 10.00 | 10.00 | 10.00 | 10.00 |

PERFORMANCE

9 Good dispensing and foam build-up; lather very thin, lacks substance; very stripping afterfeel
10 Good dispensing and foam build-up; lather very thin, lacks substance; very stripping afterfeel
11 Good dispensing and foam build-up; lather very thin, poor cleansing; mild afterfeel -continued 12 Good dispensing but foam collapses quickly; lather thin, poor cleansing; mild afterfeel; cloudy
13 Good dispensing and foam build-up; lather very thin, lacks substance, very stripping afterfeel
14 Good dispensing and foam build-up; lather good but could be denser; afterfeel not stripping
15 Good dispensing and foam build-up; lather good but could be denser; afterfeel better, more substantive; not stripping
16 Good dispensing and foam build-up; lather dense; afterfeel better, not stripping
17 Good dispensing and foam build-up; lather denser, afterfeel good, mild not stripping
18 Good dispensing and foam build-up; lather good but could be denser; afterfeel good, conditioned

EXAMPLES 19–26

The following examples were prepared to investigate the effect of water-insoluble emollients on foam, afterfeel and other physical properties.

| COMPONENT | EXAMPLE | | | | | | | |
|---|---|---|---|---|---|---|---|---|
| | 19 | 20 | 21 | 22 | 23 | 24 | 25 | 26 |
| Phase A | | | | | | | | |
| Pationic 138C (sodium lauroyl lactylate) | — | 1.00 | — | 1.00 | 1.00 | 1.00 | 1.00 | 1.00 |
| Acconon S75 (PEG 75 soy glycerides) | — | — | 1.00 | 1.00 | 1.00 | 1.00 | 1.00 | 1.00 |
| Water | 79.00 | 78.00 | 78.00 | 77.00 | 77.00 | 77.00 | 77.00 | 77.00 |
| Silquat AD or emollient** | 1.00 | 1.00 | 1.00 | 1.00 | 1.00 | 1.00 | 1.00 | 1.00 |
| Phase B | | | | | | | | |
| Standapol ES-2 (SLES 28%) | 5.00 | 5.00 | 5.00 | 5.00 | 5.00 | 5.00 | 5.00 | 5.00 |
| Bioterge AS 40 (sodium C14–16 olefin sulphonate) | 5.00 | 5.00 | 5.00 | 5.00 | 5.00 | 5.00 | 5.00 | 5.00 |
| Miranol HMA (sodium lauroamphoacetate 30%) | 10.00 | 10.00 | 10.00 | 10.00 | 10.00 | 10.00 | 10.00 | 10.00 |

PERFORMANCE

19 Good dispensing and foam build-up; lather good but could be denser; afterfeel good, conditioned
20 Good dispensing and foam build-up; lather good but could be denser; afterfeel good, more substantive, conditioned not stripped
21 Good dispensing and foam build-up; lather denser; afterfeel better, more conditioning
22 Good dispensing and foam build-up; lather denser; afterfeel excellent, conditioned and moisturized
23 Dimethicone instead of Silquat AD - dimethicone incompatible, separates into two phases
24 Dimethicone microemulsion instead of Silquat AD - disperses but depresses foam and lather build-up
25 Sunflower seed oil instead of Silquat AD - dispersed but depressed foam and lather; haze created
26 Maleated soybean oil instead of Silquat AD - separated into two phases The comparative experiments indicate that with but one exception all of these examples have good dispensing and foam build-up. However, use of anionic surfactants alone or even amphoteric surfactants alone as in Examples 9 through 13 results in a relatively very thin lather which lacks substance. These compositions also imparted a relatively harsh afterfeel with stripping of oils from the skin. Example 14 employing a combination of anionic and amphoteric surfactant however provided a relatively non-stripping afterfeel; lather was also much denser than in the earlier examples. The addition of sodium lauroyl lactylate or PEG 75 soy glycerides as in Examples 15 through 18 substantially enhanced lather and provided very good afterfeel.

Examples 23–26 demonstrate that water insoluble emollients such as dimethicone, dimethicone microemulsions, sunflower seed oil and maleated soybean oil all either depress the lather or separated out from the formulation.

The foregoing description and examples illustrate selected embodiments of the present invention. In light thereof variations and modifications will be suggested to one skilled in the art, all of which are within the spirit and purview of this invention.

What is claimed is:

1. A foaming cleansing product comprising:
   (A) a non-aerosol dispenser having:
      (i) a container for storing a cleansing composition;
      (ii) a head having a housing surrounding a pump mechanism and a foam-forming screen material;

(iii) a diptube communicating between the container and head functioning to fluidly deliver liquid cleansing composition between container and head and being upstream from the screen material; and (B) the cleansing composition being free of water insoluble emollients and comprising:

(i) from 0.1 to 50% by weight of an anionic surfactant;

(ii) from 0.1 to 30% by weight of an amphoteric surfactant having structure:

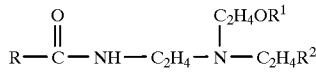

wherein R is a fatty alkyl of 6 to 22 carbons; $R^1$ is selected from the group consisting of H, $C_2H_4COOH$ and $C_2H_4COONa$; and $R^2$ is selected from the group consisting of COONa, $CH_2CHOHCH_2SO_3Na$, $C_2H_4COONa$, $CH_2COOCH_2COOH$ and $CH_2COOCH_2COONa$;

(iii) from 0.1 to 5% of a foam densifying agent which is a $C_8$–$C_{12}$ acyl lactylate;

(iv) from 0.1 to 10% by weight of a second foam densifying agent which is an ethoxylated glyceride ester.

2. The product according to claim 1 wherein the screen material is a wire gauze.

3. The product according to claim 2 wherein a second wire gauze is placed downstream from the first wire gauze, the cleansing composition being required to traverse both the first and second wire gauze to achieve a foam.

4. The product according to claim 1 wherein the amphoteric surfactant is selected from the group consisting of lauroamphoacetate and lauroamphodiacetate.

5. The product according to claim 1 wherein the lactylate is sodium lauroyl lactylate.

6. The product according to claim 1 further comprising from 0.05 to 15% by weight of a betaine.

* * * * *